(12) United States Patent
Gruber et al.

(10) Patent No.: US 7,650,187 B2
(45) Date of Patent: Jan. 19, 2010

(54) ASSEMBLY FOR WIRELESS ENERGY COMMUNICATION TO AN IMPLANTED DEVICE

(75) Inventors: Robin Gruber, Munich (DE); Thomas Schmid, Gilching (DE)

(73) Assignee: Deutsches Zentrum für Luft-und Raumfahrt e.V., Bonn (DE)

( * ) Notice: Subject to any disclaimer, the term of this patent is extended or adjusted under 35 U.S.C. 154(b) by 276 days.

(21) Appl. No.: 10/989,381

(22) Filed: Nov. 17, 2004

(65) Prior Publication Data

US 2005/0107847 A1 May 19, 2005

(30) Foreign Application Priority Data

Nov. 18, 2003 (DE) ................. 103 53 943

(51) Int. Cl.
*A61N 1/08* (2006.01)
(52) U.S. Cl. .......................... 607/33; 607/61
(58) Field of Classification Search ................ 607/60, 607/32, 61, 33; 623/3.27
See application file for complete search history.

(56) References Cited

U.S. PATENT DOCUMENTS

| | | | | |
|---|---|---|---|---|
| 3,942,535 | A * | 3/1976 | Schulman | 607/33 |
| 4,082,079 | A | 4/1978 | Rodgers | |
| 4,143,661 | A * | 3/1979 | LaForge et al. | 607/61 |
| 4,361,153 | A * | 11/1982 | Slocum et al. | 607/32 |
| 5,231,265 | A | 7/1993 | McCleer et al. | |
| 5,279,292 | A | 1/1994 | Baumann et al. | |
| 5,350,413 | A * | 9/1994 | Miller | 607/61 |
| 5,702,431 | A * | 12/1997 | Wang et al. | 607/61 |
| 5,733,313 | A * | 3/1998 | Barreras et al. | 607/33 |
| 5,759,199 | A * | 6/1998 | Snell et al. | 607/60 |
| 5,769,877 | A | 6/1998 | Barreras, Sr. | |
| 6,067,474 | A * | 5/2000 | Schulman et al. | 607/57 |
| 6,597,076 | B2 | 7/2003 | Scheible et al. | |
| 6,651,999 | B1 | 11/2003 | Fischer et al. | |

(Continued)

FOREIGN PATENT DOCUMENTS

DE 41 32 557 A1 7/1993

(Continued)

OTHER PUBLICATIONS

Richard P. Phillips, "A Transcutaneous Energy Transport System with Voltage Input Power Control" Annual International Conference of the IEEE Engineering in Medicine and Biology Society, vol. 13, No. 5, 1991; pp. 2131-2132.

(Continued)

*Primary Examiner*—Angela D Sykes
*Assistant Examiner*—Joseph Stoklosa
(74) *Attorney, Agent, or Firm*—Browdy and Neimark, PLLC

(57) ABSTRACT

An assembly for wireless energy communication to an implanted device comprises an external belt (7) accommodating a wearer control (1) followed by controller (2), a battery pack (4), an inverter (3), a transmission coil (8) connected in parallel by a plurality of capacitors, and an infrared transceiver 9. Provided furthermore is an implanted device comprising a receiver coil (11) having the same dimensions as the transmission coil (8), a rectifier following said receiver coil (11), an infrared transceiver (10) followed by a controller and an sensor assembly (17) assigned thereto as well as a battery pack (16) for powering said implanted device via an energy manager (14).

18 Claims, 4 Drawing Sheets

U.S. PATENT DOCUMENTS

| | | | |
|---|---|---|---|
| 7,295,878 B1 * | 11/2007 | Meadows et al. | 607/61 |
| 2002/0154518 A1 | 10/2002 | Elferich et al. | |
| 2003/0014087 A1 * | 1/2003 | Fang et al. | 607/48 |

FOREIGN PATENT DOCUMENTS

| | | |
|---|---|---|
| DE | 41 04 359 A1 | 1/1994 |
| DE | 196 17 102 A1 | 10/1997 |
| DE | 199 15 487 C1 | 11/2000 |
| DE | 101 19 283 A1 | 10/2002 |
| DE | 199 46 934 A1 | 11/2003 |
| GB | 2 239 802 A | 7/1991 |
| JP | 2002-1 98 873 A | 7/2002 |
| WO | 9507109 A1 | 3/1995 |
| WO | 9508365 A1 | 3/1995 |
| WO | 99/42173 A1 | 8/1999 |
| WO | 01/37926 A1 | 5/2001 |
| WO | 01/85250 A1 | 11/2001 |

OTHER PUBLICATIONS

G. B. Bearnson et al., "Electronic Development for the Utah Electrohydraulic total Artificial Heart", University of Utah Artificial Heart Research Laboratory, Sixth Annual IEEE Symposium on Computer-Based Medical Systems; 1993; pp. 247-25.

C. Tsai et al., "Design of Wireless Transcutaneous Energy Transmission System for Totally Artificial Hearts" Department of Electrical Engineering, National Cheng Kung University, IEEE 2000; pp. 646-649.

Tofy Mussivand, Ph.D et al., "HeartSaver VAD: A totally Implantable Ventricular Assist Device. Results of In Vivo Studies", The Journal of Extra-Corporeal Technology, vol. 32, No. 4, Dec. 2000, pp. 184-189.

R. Puers et al., "Recent Progress on Transcutaneous Energy Transfer for Total Artificial Heart Systems", 2002.

Aly El-Banayosy et al., "Long-term implantable left ventricular assist devices: out-of-hospital program", Cardiology Clinics 21 (2003), pp. 57-65.

T. Mussivand et al., "A remotely controlled and powered artificial heart pump", Artif Organs, Dec. 20, 1996 (12) 1314-9.

T. Mussivand et al., "Transcutaneous energy transfer with voltage regulation for rotary blood pumps", Artif Organs, Jun. 20, 1996 (6) 621-4.

T. Mussivand et al., "A transcutaneous energy and information transfer system for implanted medical devices", AIO J. Jul.-Sep. 1995 M253-8.

T. Mussivand et al., "Transcutaneous energy transfer system performance evaluation", Artif Organs, Nov. 17, 1993 (11) 940-7.

* cited by examiner

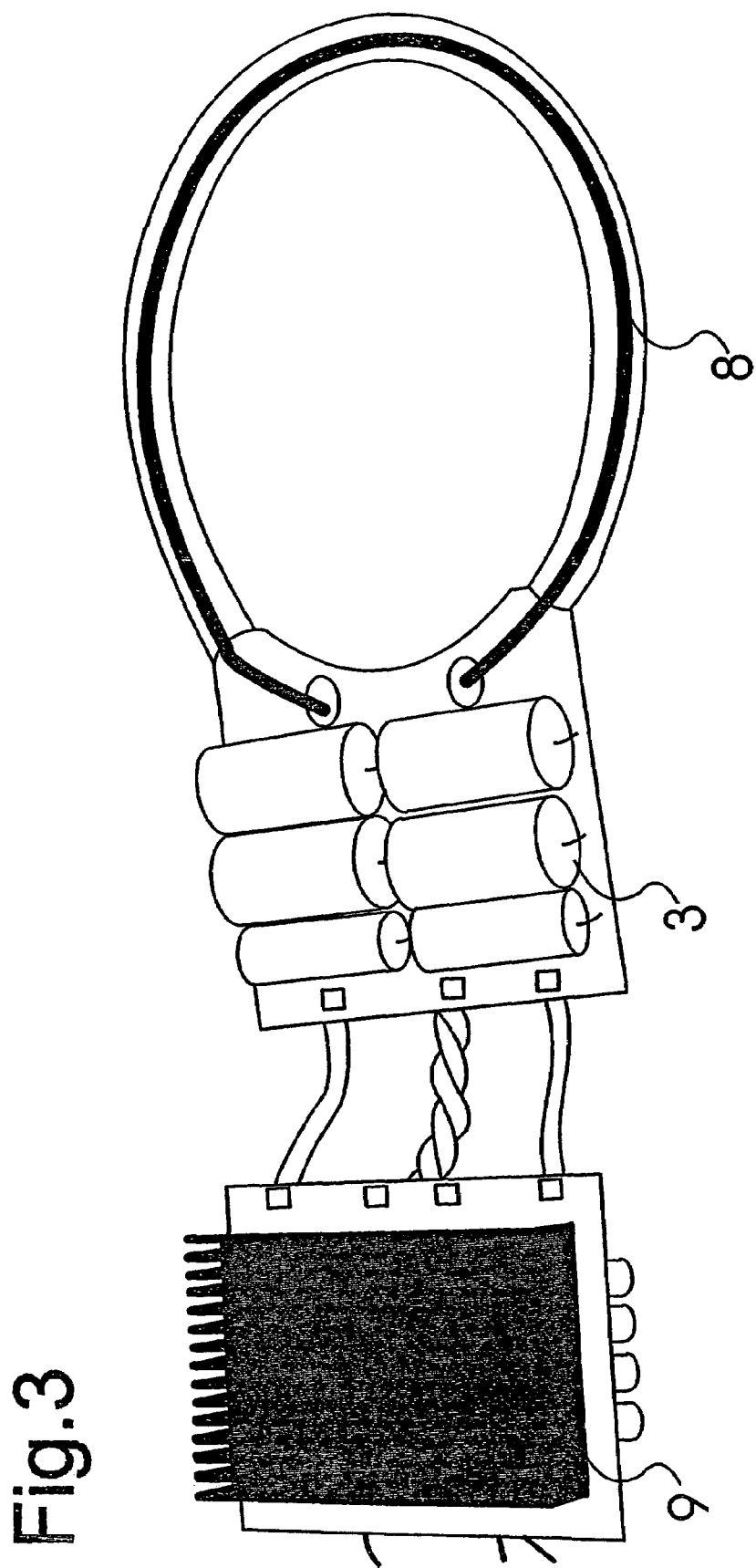

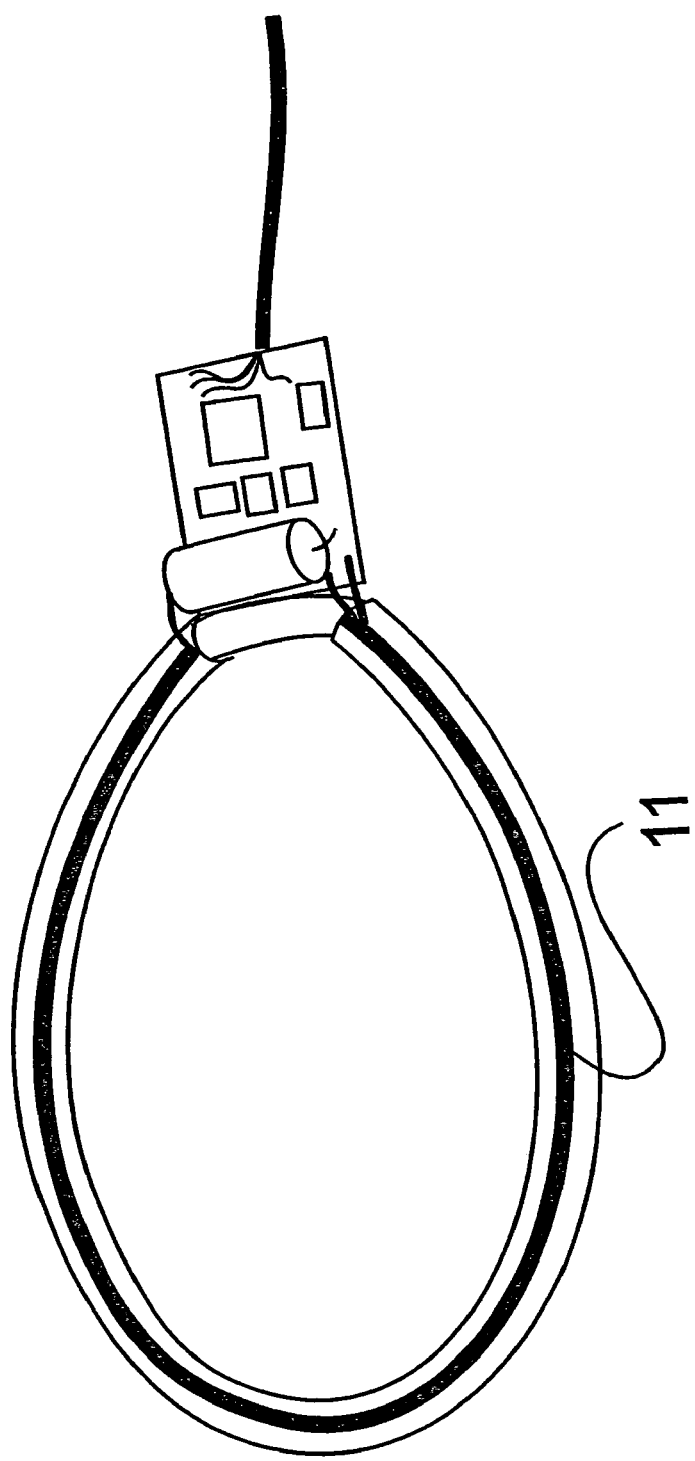

ASSEMBLY FOR WIRELESS ENERGY COMMUNICATION TO AN IMPLANTED DEVICE

FIELD OF THE INVENTION

The invention relates to an assembly for wireless energy communication to an implanted device such as for instance a cardiac support system or artificial heart.

PRIOR ART

One major problem in achieving artificial organ or other implanted systems is their power supply. Where devices having a low power consumption such as for instance cardiac pacemakers are concerned, the energy can be supplied via batteries. For the supply of more powerful devices the following systems have hitherto found application:
- a direct supply wired through the abdominal wall or in the region of the neck, albeit with the risk of a permanent source of inflammation focused about the point of insertion and low acceptance by the wearer because of life quality impairment due to, for example, taking a shower or swimming no longer being possible, the risk of serious internal injuries due to inadvertent tugging of the wiring, etc,
- inductive systems making use of a high-frequency alternating magnetic field for energy communication as known in the following variants:

a) Use of two relatively small coils in conjunction with two ferrite core halves separated by a narrow (air) gap in which the skin can be located. The good magnetic coupling when closely spaced permits downsizing the coils. However, when the spacing becomes larger, i.e. as of approx. 10 mm, the coupling quickly deteriorates requiring the system to be implanted directly subcutaneous. Apart from this, the transmitter and receiver parts always need to be positioned precisely one above the other, otherwise the coupling quickly deteriorates. On top of this, the core or receiver coil is a heavy, rigid foreign body for the wearer.

b) A system incorporating a non-ferrous, spiral-wound transmitter and receiver coil. In this case, however, to ensure adequate power communication, either both coils need to be tuned with the aid of capacitors to (practically) a common resonance or frequency compliance is done without checking the frequency range. The drawback of this assembly is that a spiral-wound coil is not optimal as regards the reach of magnetic field and that although the coils as compared to the assembly with ferrite cores are lighter, they have a larger footprint in thus resulting in a substantially rigid foreign body for the wearer of such a system. In this system too, a change in the spacing alters the coupling, resulting in the resonant frequencies of the transmitter and receiver becoming out of tune, so that in this case too, precise positioning of the transmitter coil and receiver coil is mandatory.

SUMMARY OF THE INVENTION

It is thus the object of the invention to provide an assembly for wireless energy communication to an implanted device comprising a consistent power supply complying with the energy requirement.

This object is achieved by an assembly for wireless energy communication to an implanted device having the features according to the present invention.

The assembly in accordance with the invention comprises an external belt accommodating a wearer control followed by a controller, a battery pack, an inverter, a transmitter coil circuited in parallel by a plurality of capacitors, and an infrared transceiver. An implanted device in accordance with the invention comprises a receiver coil sized the same as the transmitter coil and followed by a rectifier, an infrared transceiver followed by a controller and a sensor module assigned thereto, as well as a battery pack for powering the implanted device via an energy manager.

In accordance with a preferred aspect of the invention the transmitter coil is configured with few, preferably three, windings each comprising a plurality of approx. 600 to 800, preferably 720 wires each insulated from the other and each having a wire gauge in the region of 0.1 mm and having the shape of an oval ring.

In accordance with the invention the receiver coil is the same size as the transmitter coil and likewise comprises a large number of preferably twelve (possibly center-tapped) windings, each formed preferably by 100 to 150 wires of copper, thus resulting in the receiver coil being highly flexible.

Of particular advantage in the assembly in accordance with the invention is the AUTO compliance of power and frequency whilst ensuring maintenance of a desired frequency band, the internal energy storage in thus making a constant voltage available, the use of flexible ring coils for enhanced implantation and the possibility of duplex information communication between an implant and an external wearer control. This is assured particularly by an optimum coil configuration and AUTO compliance of the transmitted power and communication frequency in a restricted frequency band, whilst eliminating most of the problems as cited above.

DESCRIPTION OF THE DRAWINGS

The invention will now be detailed with reference to the drawing in which:

FIG. 3 is an illustration of one embodiment of an inverter and a transmitter coil, and FIG. 4 is a diagrammatic illustration of a receiver coil followed by the electronics module.

DESCRIPTION OF THE INVENTION

Figure 1:
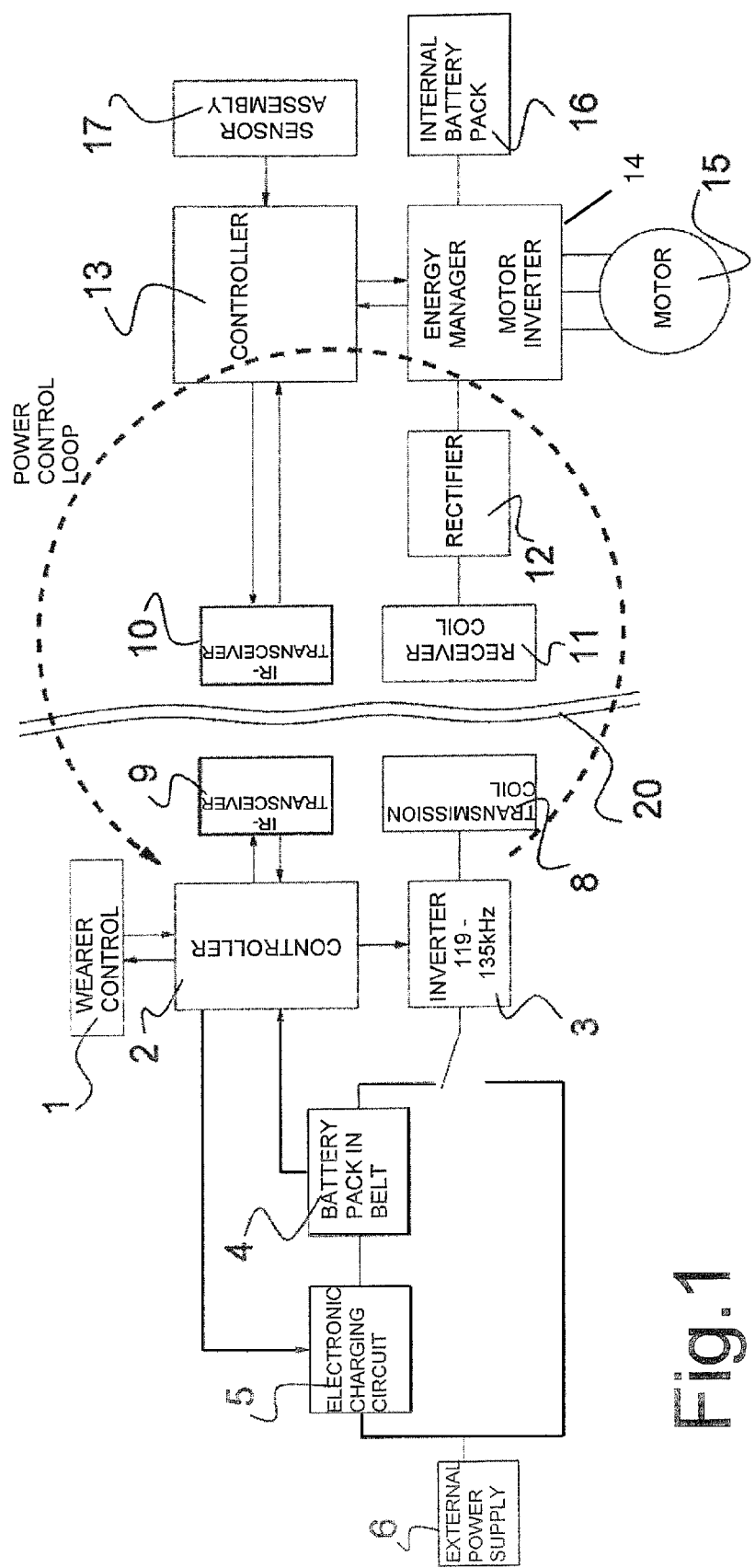
FIG. 1 is block diagram showing the components of an assembly for wireless energy communication by means of a power control loop.

Referring now to FIG. 1 there is illustrated one embodiment of an assembly for wireless energy communication comprising a belt 7 (FIG. 2) accommodating a wearer control 1 to which a controller 2 is assigned for controlling an inverter 3, a transmission coil 8 as well as an infrared transceiver 9. Furthermore accommodated in the belt 7 for charging the battery pack 4 is an electronic charging circuit 5. By means of an external power supply 6 the battery pack 4 can be charged via the electronic charging circuit 5.

An implanted/implantable device comprises an infrared transceiver 10 to which a controller 13 as well as a sensor assembly 17 is assigned. Via the controller 13 an energy manager 14 and an inverter assigned to a motor 15 are controlled. The energy manager 14 is powered by an internal battery pack 16. The energy manager 14 is connected to a receiver coil 11 by a rectifier 12.

The components assigned to a power control loop are encircled by the broken line. Furthermore indicated in FIG. 1 by two wavy lines is an abdominal wall 20.

Figure 2:
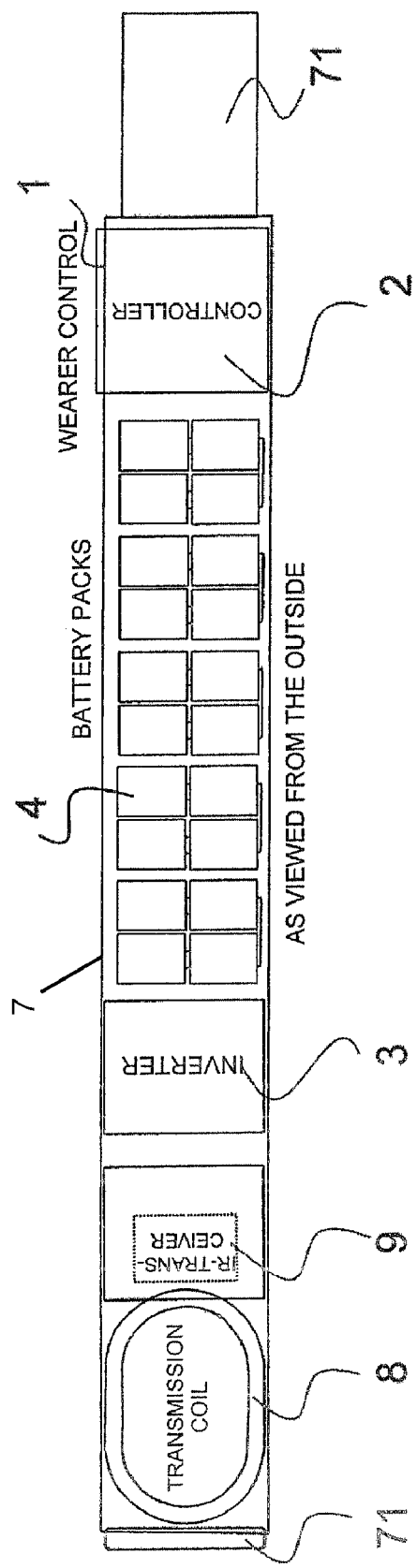
FIG. 2 is a diagrammatic illustration of one possible variant of an abdominal belt.

Referring now to FIG. 2 there is illustrated diagrammatically the belt 7 roughly 100 mm wide, for example, and provided with clasps 71 at both ends. The components represented in FIGS. 1 and 2 are shown uncased, it being understood, of course, that each of the implantable parts is sheathed in a body-compatible material such as silicone.

Via the wearer control 1 simple control functions are entered for the implant and the status indicated or retrieved via a display. A processor in the wearer control 1 ensures satisfactory communication and analysis of the signals transmitted by infrared from the transmission coil 8 to infrared transceiver 10 and vice-versa and thus to and from the implant. Furthermore this processor-controls the frequency and power of the HF inverter 3, it likewise monitoring fast charging of the battery pack 4 accommodating in the belt 7 to ensure cordless operation for roughly one hour depending on the power consumption of the implant.

The inverter 3 converts the battery voltage of 20 to 28V by means of a MOSFET full bridge rectifier into an AC voltage having the frequency and pulse width as dictated by the processor. The communication frequency range is preferably from 119 to 135 kHz. To avoid noise in the switching edges this AC voltage is applied symmetrically via two serial inductances to the oscillator circuit of the transmission coil 8. Provided furthermore are a current limiter, an over temperature cut out and an output voltage limiter.

Serving for the actual communication of energy is the transmission coil 8 parallel circuited with very low impedance polypropylene capacitors having a total capacitance of approx. 1 µf as the oscillator circuit for the frequency band in the range 119 to 135 kHz so that even with poor coupling sufficient energy can be communicated.

The transmission coil 8 preferably consists of three windings, each comprising 720 wires of copper, each insulated from the other and each having a wire gauge of 0.1 mm. The windings are sheathed in a tube of body-compatible material such as silicone. For a small footprint the transmission coil 8 is optimally ovally configured ring-shaped so that the overall dimensions are of the order of approx. 150×100 mm (see FIG. 3).

The assembly of the transmission coil 8 circuited in parallel by the capacitors makes for a high Q since the copper wires each insulated from the other and together with the capacitors form a low impedance oscillator circuit. In addition, the transmission coil 8 is highly flexible in thus enhancing the wearing comfort of the belt 7 as a whole.

The receiver coil 11 has the same footprint as the transmission coil 8, it preferably comprising twelve centre tapped windings and each made up of preferably 120 separate wires. Here too, a polypropylene capacitor may be circuited in parallel between the middle and end or between both ends of the coil and having a capacitance in the range 47 nF to 100 nF forms an oscillator circuit tuned to the resonant frequency which is two to five times that of the working frequency and thus far above the latter, it thus suffering no serious mistuning when there is a change in the spacing to the oscillator circuit of the transmitter. The field which is very strong because of the transmitter resonance is sufficient, however, to couple-in adequate power even when the receiver is poorly tuned.

The balanced AC voltage materializing at the ends of the coil is rectified via separate diodes or synchronization rectifier and charges via an inductance a filter capacitor of the connected implant electronics module. It is due to this inductance that the current flow angle is maintained wide enough in minimizing the diode power loss.

The same as the transmission coil 8, the receiver coil 11 too is sheathed in a tube of body-compatible material such as silicone. The body-compatibility of the receiver coil 11 is greatly enhanced by its flexibility and by it being configured as an oval-shaped ring, resulting in hardly any tissue being cut off from a blood supply and the receiver coil 11 is able to conform to movements of the body. As tests have shown, neither the transmitter coil nor the receiver coil exhibits any appreciable increase in temperature.

Located very near to the transmission coil 8 and receiver coil 11 in each case is a half-duplex infrared communication module in the form of the infrared transceiver 9 and 10 ensuring good communication between the implant electronics module and the wearer control 1 at approx. 115 kbit/s. This module is magnetically shielded to ensure safe operation even in the presence of a high magnetic field strength.

In addition to filter capacitors for smoothing and buffering the communicated power the implant electronics module also comprises a pack of e.g. twenty nickel metal hydride (NiMH), LiION or similar rechargeable batteries for supplying the implant with energy when there is a mains power failure. In addition integrated is a processor connected to motor drivers for activating the motor, speed control, sensor analysis, charging the batteries and monitoring their voltage as well as data communication.

Furthermore provided is a buzzer to alert the wearer to critical operational situations such as a battery requiring recharging, even without the wearer control 1.

In addition to monitoring the temperature as a safeguarding function, the implant electronics module also includes a relay with the aid of which the receiver coil 11 can be disconnected should there be a fault in the transmitter unit 8 and more energy than required is transmitted.

A further relay disconnects the battery pack to thus make it possible to shelve the electronics module without the rechargeable batteries discharging, these not being reconnected until activated by an external power supply. In addition, this safeguards the energy storage from a hazardous drain by it being disconnected on low voltage.

Yet a further special feature of the assembly in accordance with the invention is the way the energy communication functions by supplying only as much energy as is required by the implant electronics module, in thus enabling losses of the energy transmission system to be minimized. For this purpose the control loop as described in the following is made use of, assuming that the implant electronics module has a positive internal resistance.

The implant electronics module continually measures the voltage made available to it, compares it to the required voltage and communicates this information via the infrared interface to the wearer control 1. When, for instance, a higher voltage is needed for charging an almost fully charged battery than the voltage for charging a battery which is almost drained, the pulse width of the transmitter frequency is increased or reduced via the wearer control 1 so that correspondingly more or less power is communicated. The buffer capacitors of the implant electronics module are dimensioned large enough so that even in the case of a voltage spike, the drop or increase in voltage can be maintained small during the dead time produced by data communication until the transmitter part supplies more power.

Aside from disturbances caused by a change in load, changes in the spacing of the transmission coil 8 from the receiver coil 11, for example due to respiration, may change the coupling, resulting in the oscillator circuit of the transmission coil 8 being additionally mistuned. The risk of this happening is counteracted by the processor of the wearer control 1 continually searching for the optimum communication frequency.

For this purpose, the frequency at any one time is varied in one direction. At the same time the transmitter power is measured, as is necessary so that the receiver in the form of the receiver coil 11 receives enough energy, the minimum value of which is stored. As soon as the transmitter power required drops below this minimum value, the direction of variation is reversed (maximum power-point tracking).

Since this tracking is done exclusively by the software, it is assured that the desired frequency band is not exceeded which is something that is difficult to guarantee with a self-induced oscillator. The large coil diameter permits achieving ranges up to 30 mm and a power of up to approx. 60 Watt.

In addition to energy management as already described, the implant electronics module also handles the task of charging the nickel metal hydride (NiMH) or LiION battery pack, it only taking roughly 2 hours to fully charge this battery pack by means of a delta-peak/theta timeout.

In the absence of an external power supply, for instance when the wearer is taking a shower, the internal battery pack is capable of powering the connected motor for a minimum of 30 minutes depending on the power required and type of battery pack in each case. The wearer is alerted by a beeper should the charging level of the battery pack become critical. In addition, sensors can be connected both as digital Hall sensors for operating the motor and as analogue sensors, such as pressure sensors.

Likewise provided is an interface for communicating with a cardiac pacemaker. With cardiac support systems this interface permits synchronization to the heartbeat or—where an irregular heartbeat is involved—synchronization of the cardiac muscle to the cardiac support system.

What is claimed is:

1. An assembly for wireless energy communication to an implantable device configured to be implanted in a wearer, comprising:
   an external belt configured to accommodate a first plurality of elements, the first plurality of elements comprising:
      a wearer control;
      a first controller connected to the wearer control;
      a first battery pack for normally supplying power to and directly powering the implantable device;
      an inverter operatively connected to and controlled by the first controller;
      a transmission coil for transmitting the power supplied by the battery pack and connected in parallel to a plurality of capacitors; and
      an infrared transceiver; and
   the implantable device comprising an implant electronics module comprising:
      a receiver coil having the same dimensions as said transmission coil configured to receive the power transmitted by the transmission coil;
      a rectifier operatively connected to said receiver coil;
      an infrared transceiver;
      a second controller operatively connected to the infrared transceiver;
      a sensor assembly assigned and operatively connected to the second controller;
      an energy manager operatively connected to the rectifier; and
      a second battery pack operatively connected to the energy manager for powering said implantable device responsive to the energy manager in the absence of power being supplied by the first battery pack;
   wherein said wearer control comprises a display and a processor for faultless communication and analysis of data signals for controlling the frequency and power of the inverter that are communicated by infrared to and from said implantable device;
   wherein said transmission coil is operable at a field strength that is regulated at said implanted device;
   wherein the implant electronics module continually measures the voltage made available to it, compares the measured voltage to a required voltage, and transmits the measured voltage and comparison results to the wearer control, such that only a sufficient amount of energy is communicated to said implantable device to operate said implanted device.

2. The assembly as set forth in claim 1, wherein said inverter is an HF inverter and the assembly further comprises a MOSFET transistor power bridge for converting the voltage of said first battery pack into an AC voltage having a frequency and pulse width as dictated by the processor of said wearer control.

3. The assembly as set forth in claim 1, wherein said transmission coil comprises a few windings each comprising a plurality of wires each insulated from the other.

4. The assembly as set forth in claim 3, wherein said transmission coil comprises three windings each comprising approx. 600 to 800 separate wires of copper each insulated from the other.

5. The assembly as set forth in claim 4, wherein each of said three windings comprises 720 wires of copper each insulated from the other, each having a wire gauge in the region of 0.1 mm.

6. The assembly as set forth in claim 1, wherein said transmission coil is configured as an oval-shaped ring.

7. The assembly as set forth in claim 6, wherein said oval-shaped transmission coil has outer dimensions in the region of 100 mm×150 mm.

8. The assembly as set forth in any of the preceding claims, further comprising very low impedance capacitors having a total capacitance of 1 µF, wherein said transmission coil is circuited in parallel by the very low impedance capacitors.

9. The assembly as set forth in claim 1, wherein said receiver coil comprises a larger number of center tapped windings than said transmission coil.

10. The assembly as set forth in claim 1, wherein said receiver coil comprises twelve center-tapped windings each comprising 100 to 150 wires of copper.

11. The assembly as set forth in claim 1, wherein said receiver coil is configured flexible.

12. The assembly as set forth in claim 1, further comprising a capacitor having a capacitance of 47 to 100 µF circuited in parallel between middle and end or both ends of said receiver coil.

13. The assembly as set forth in claim 12, wherein said capacitor is a polypropylene capacitor.

14. The assembly as set forth in claim 1, wherein both said transmission coil and said receiver coil are sheathed in a tube of body-compatible material.

15. The assembly as set forth in claim 14, wherein said body-compatible material is silicone.

16. The assembly as set forth in claim 1, wherein the infrared transceiver in the external belt and the infrared transceiver in the implantable device forms a half-duplex infrared communication device in the region of said transmission coil and receiver coil.

17. The assembly as set forth in claim 1, wherein the implant electronics module comprises an audible sound device for emitting an audible warning signal for alerting the wearer to critical operational situations.

18. The assembly as set forth in claim 1, wherein the wearer control is operable to increase or reduce the pulse of the transmitter frequency responsive to the measured voltage and the comparison results transmitted to the wearer control indicating that the battery is almost fully charged, or is almost drained so that correspondingly more or less power is communicated.

* * * * *

UNITED STATES PATENT AND TRADEMARK OFFICE
CERTIFICATE OF CORRECTION

| | | |
|---|---|---|
| PATENT NO. | : 7,650,187 B2 | Page 1 of 1 |
| APPLICATION NO. | : 10/989381 | |
| DATED | : January 19, 2010 | |
| INVENTOR(S) | : Gruber et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 468 days.

Signed and Sealed this

Twenty-third Day of November, 2010

David J. Kappos
*Director of the United States Patent and Trademark Office*